United States Patent
Guala

(10) Patent No.: US 8,701,696 B2
(45) Date of Patent: Apr. 22, 2014

(54) DEVICE FOR THE CONTROLLED SUPPLY OF A LIQUID TO A MEDICAL FLOW LINE

(75) Inventor: Gianni Guala, Turin (IT)

(73) Assignee: Industrie Borla S.p.A., Moncalieri (Torino) (IT)

(*) Notice: Subject to any disclaimer, the term of this patent is extended or adjusted under 35 U.S.C. 154(b) by 215 days.

(21) Appl. No.: 13/378,548

(22) PCT Filed: Jun. 10, 2010

(86) PCT No.: PCT/IB2010/052583
§ 371 (c)(1),
(2), (4) Date: Mar. 5, 2012

(87) PCT Pub. No.: WO2010/146506
PCT Pub. Date: Dec. 23, 2010

(65) Prior Publication Data
US 2012/0152392 A1     Jun. 21, 2012

(30) Foreign Application Priority Data
Jun. 15, 2009   (IT) .............................. TO2009A0455

(51) Int. Cl.
*E03D 9/03*     (2006.01)

(52) U.S. Cl.
USPC ........ 137/205.5; 251/149.9; 604/85; 604/407

(58) Field of Classification Search
CPC .. A61M 5/1409; A61J 1/2096; B01F 15/0212
USPC ................. 137/205.5, 268; 604/85, 407, 411; 222/81; 251/149.9
See application file for complete search history.

(56) References Cited

U.S. PATENT DOCUMENTS

| 3,202,164 A | * | 8/1965 | Thompson et al. ...... 137/101.11 |
| 4,534,758 A | | 8/1985 | Akers et al. |
| 5,547,471 A | * | 8/1996 | Thompson et al. ............. 604/87 |
| 5,913,327 A | * | 6/1999 | Zhadanov et al. ......... 137/205.5 |
| 6,296,621 B1 | * | 10/2001 | Masuda et al. ................... 604/89 |
| 7,690,392 B1 | * | 4/2010 | Sarkiss ...................... 137/205.5 |
| 2007/0106244 A1 | | 5/2007 | Mosler et al. |

FOREIGN PATENT DOCUMENTS

| EP | 0163387 A1 | 12/1985 |
| EP | 0246715 A2 | 11/1987 |
| WO | 2008126090 A1 | 10/2008 |

OTHER PUBLICATIONS

International Search Report for PCT/IB2010/052583 dated Nov. 11, 2010.

* cited by examiner

*Primary Examiner* — John Rivell
*Assistant Examiner* — Reinaldo Sanchez-Medina
(74) *Attorney, Agent, or Firm* — Heslin Rothenberg Farley & Mesiti, P.C.; Victor A. Cardona, Esq.

(57) ABSTRACT

A device for the controlled supply of a liquid within a medical flow line, includes a retaining body rotatable on an intermediate tubular connector arranged between a tubular inlet connector and a tubular outlet connector of a primary liquid and within which a bottle pierceable and containing a secondary liquid can be fitted. The retaining body includes a hollow piercing spike, rotation blocking means of the retaining body disengageable following insertion of the bottle, axial stop means of the inserted bottle, and progressive opening means of a flow passage from the hollow spike to a flow line of the primary liquid during the rotation of the retaining body with the bottle inserted therein from a first angular position of complete closure to a second angular position of complete opening.

17 Claims, 8 Drawing Sheets

DEVICE FOR THE CONTROLLED SUPPLY OF A LIQUID TO A MEDICAL FLOW LINE

CROSS REFERENCE TO RELATED APPLICATIONS

Figure 1:
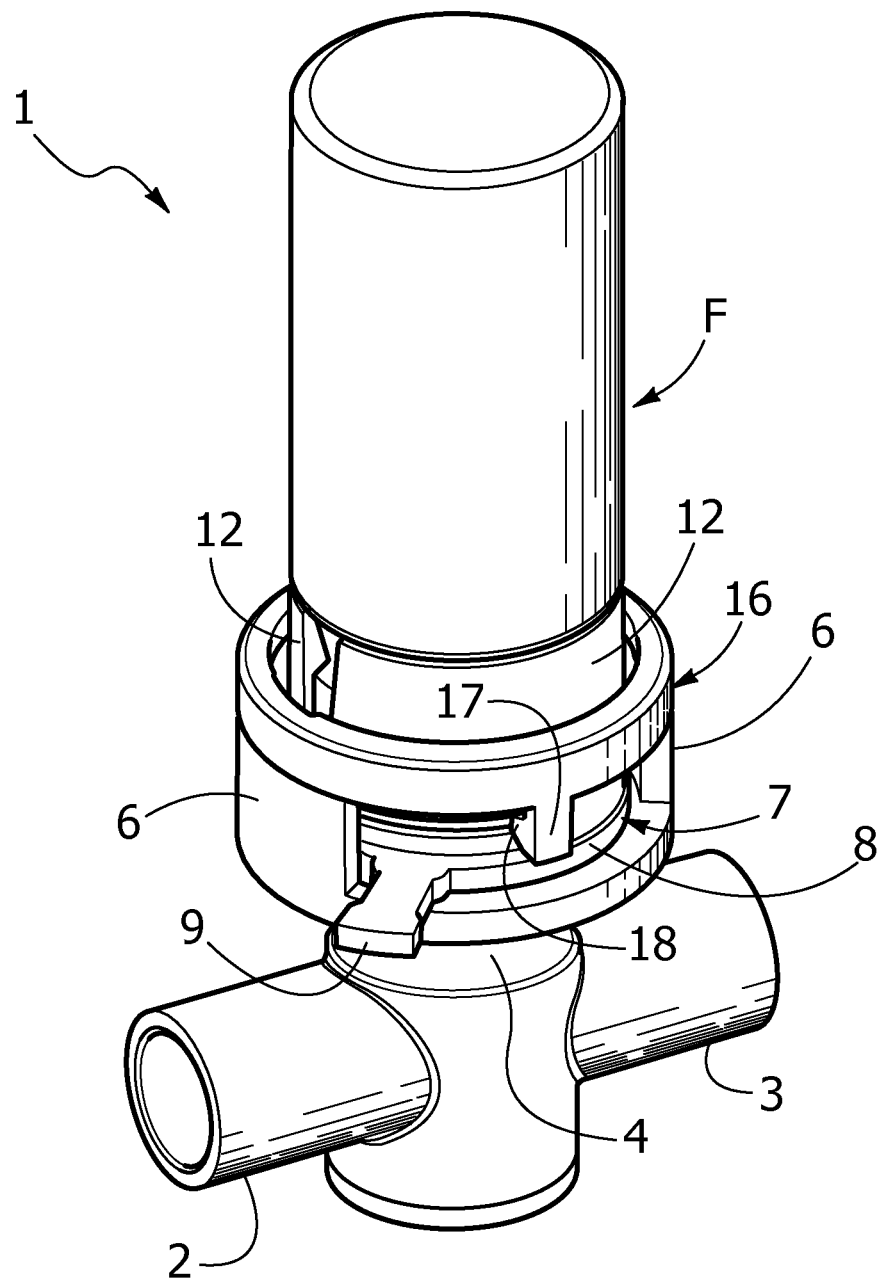

This application is a national stage of PCT International Application No. PCT/IB2010/052583 filed on Jun. 10, 2010, and published in English on Dec. 23, 2010 as WO 2010/146506, which claims priority to Italian patent application number TO2009A000455 filed on Jun. 15, 2009, the entire disclosures of which are incorporated herein by reference.

FIELD OF THE INVENTION

The present invention generally refers to medical flow lines, particularly but not exclusively haemodialysis lines.

In particular the invention refers to medical flow lines including a tubular inlet connector and a tubular outlet connector defining a flow line of a primary liquid and an intermediate tubular transverse connector arranged therebetween for the introduction of a secondary liquid into la flow line.

PRIOR ART

Typically, simple syringes, whose needle is capable of piercing an elastic diaphragm sealingly secured to the intermediate connector are used for the introduction of the secondary liquid through the intermediate tubular connector, to provide the controlled supply thereof into the flow of primary liquid. The liquid to be supplied, typically contained within a bottle, vial or the like provided with a pierceable cap, must be preliminarily extracted by inserting the needle of the syringe through the pierceable cap and then suctioning it into the syringe. Then, the liquid contained in the syringe is injected into the intermediate connector following piercing of the relative cap.

These operations require the intervention of a skilled operator, in particular during the injection step to activate the syringe plunger by means of pressure calibrated as a function of the desired supply velocity of the secondary liquid within the primary liquid flow.

An alternative to the normal syringes is constituted by syringes or more generally by needleless supply devices which, though suitable to guarantee easier supply of the secondary liquid, are relatively more expensive and require a preliminary step of drawing the secondary liquid from the relative bottle.

SUMMARY OF THE INVENTION

The object of the present invention is that of overcoming the abovementioned drawbacks, and provide a device for the controlled supply of a liquid into a medical flow line of the previously described type which does not require using syringes and allows introducing the secondary liquid into the flow line of the primary liquid, in an easily controllable manner, directly from the bottle or the like without requiring preliminary extraction of the secondary liquid from the relative bottle.

This object is attained according to the invention due to a device for controlled supply essentially characterised in that the intermediate connector comprises an annular stationary base on which a hollow retaining body within which said bottle or the like can be inserted rotatable, coaxially to the intermediate connector, the retaining body including:

a hollow axial spike designed to pierce said pierceable cap when said bottle or the like is fitted into the hollow retaining body, said spike having an inner flow passage usually closed towards said intermediate connector, rotation blocking means of the retaining body relative to said annular base in a first angular position, said blocking means being disengageable by said bottle or the like as a result of insertion thereof into said retaining body, axial stop means of said bottle or the like designed to be activated following rotation of the retaining body starting from said first angular position, and progressive opening means of said flow passage of said spike towards said intermediate connector during the rotation of said retaining body from said first angular position, in which communication between said flow passage and said intermediate connector is completely closed, towards a second angular position in which such communication is completely open.

Due to this solution idea, the controlled supply of the liquid contained within the bottle or the like may be activated in a simple and safe manner directly therefrom, without requiring syringes and even by non-highly-skilled personnel.

According to a preferred embodiment of the invention the retaining body further comprises a shifting member axially projecting, within the flow line of the primary liquid, at the side opposite to the hollow spike. The shifting member is rotatable along with the retaining body between a position of substantial non-obstruction of the liquid of the primary liquid, corresponding to said first angular position of the hollow body, and a position of substantial obstruction of the primary liquid flow, corresponding to said second angular position of the hollow body. In such case, the flow passage of the hollow spike conveniently has two parallel ducts located at sides opposite to the abovementioned shifting member.

According to another aspect of the invention the abovementioned progressive opening means of the device include a pair of variable-section passages formed in said intermediate connector and a pair of bores each communicating with a respective duct of said hollow spike and rotatable along with said retaining body to cooperate with the abovementioned variable-section passages.

Such progressive communication means are completely closed in the first angular position of the hollow body and they are opened completely in the second angular position of the hollow body.

BRIEF DESCRIPTION OF THE REPRESENTATIONS

Figure 2:
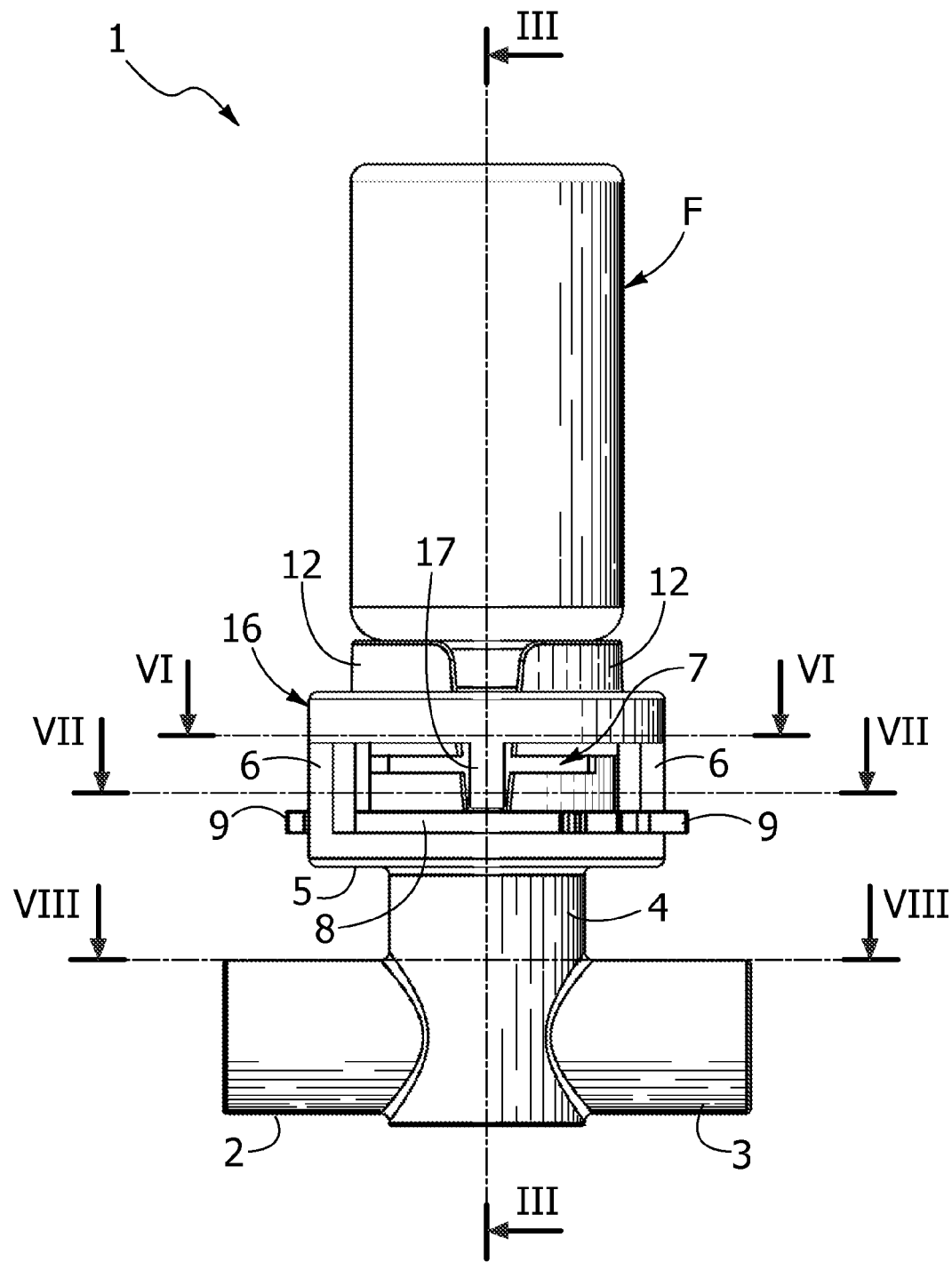
Figure 3:
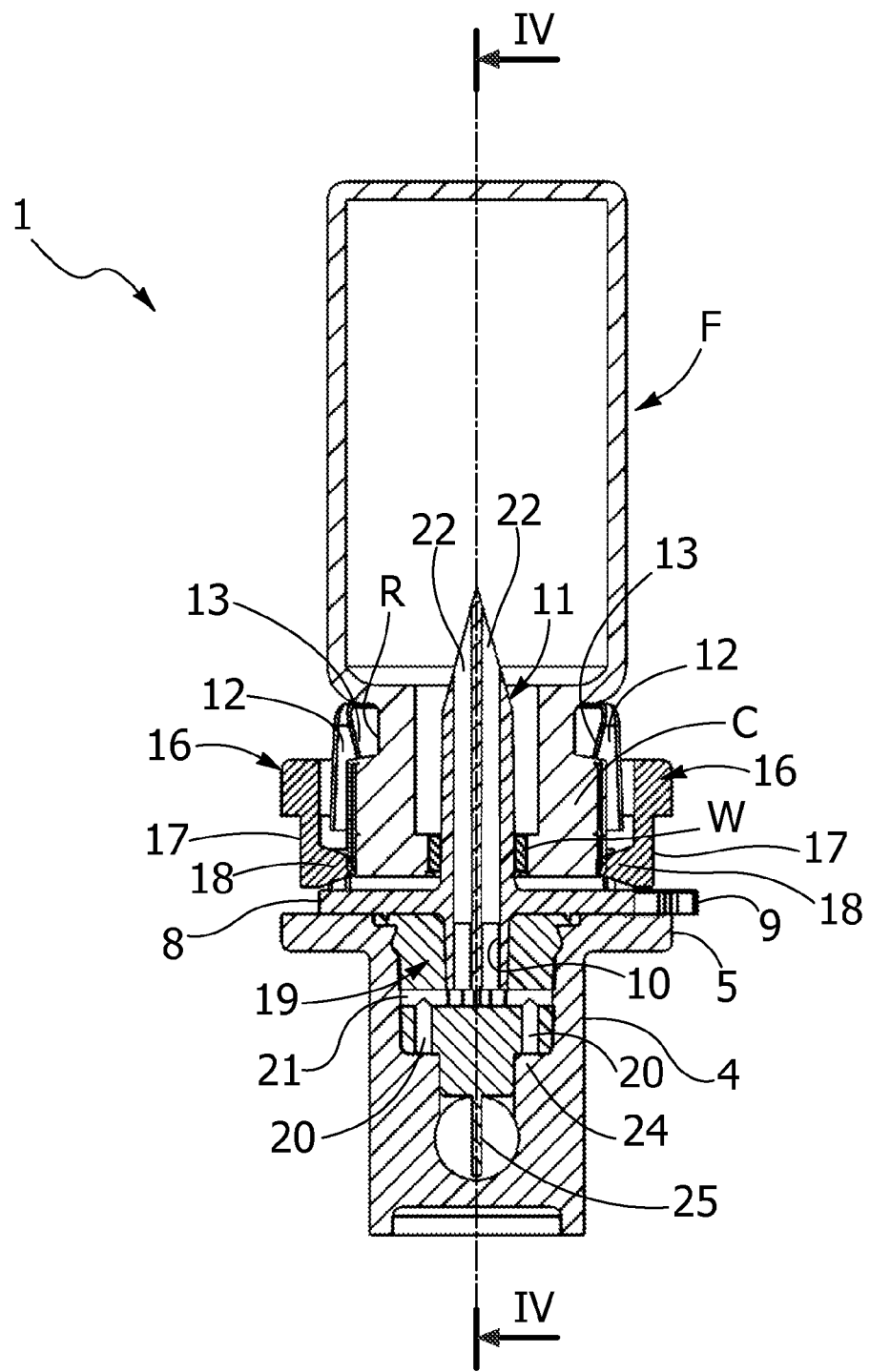
Figure 4:
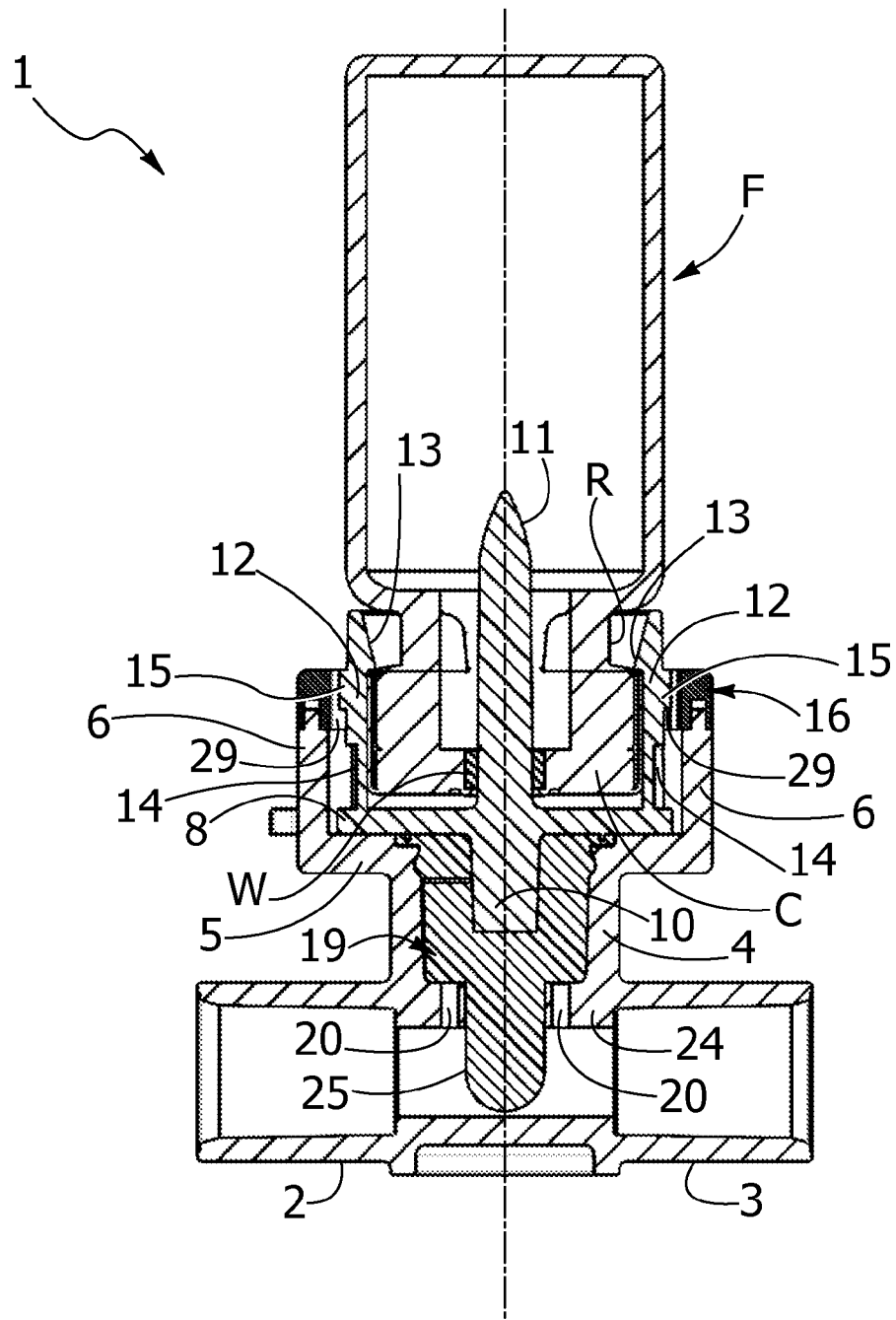
Figure 5:
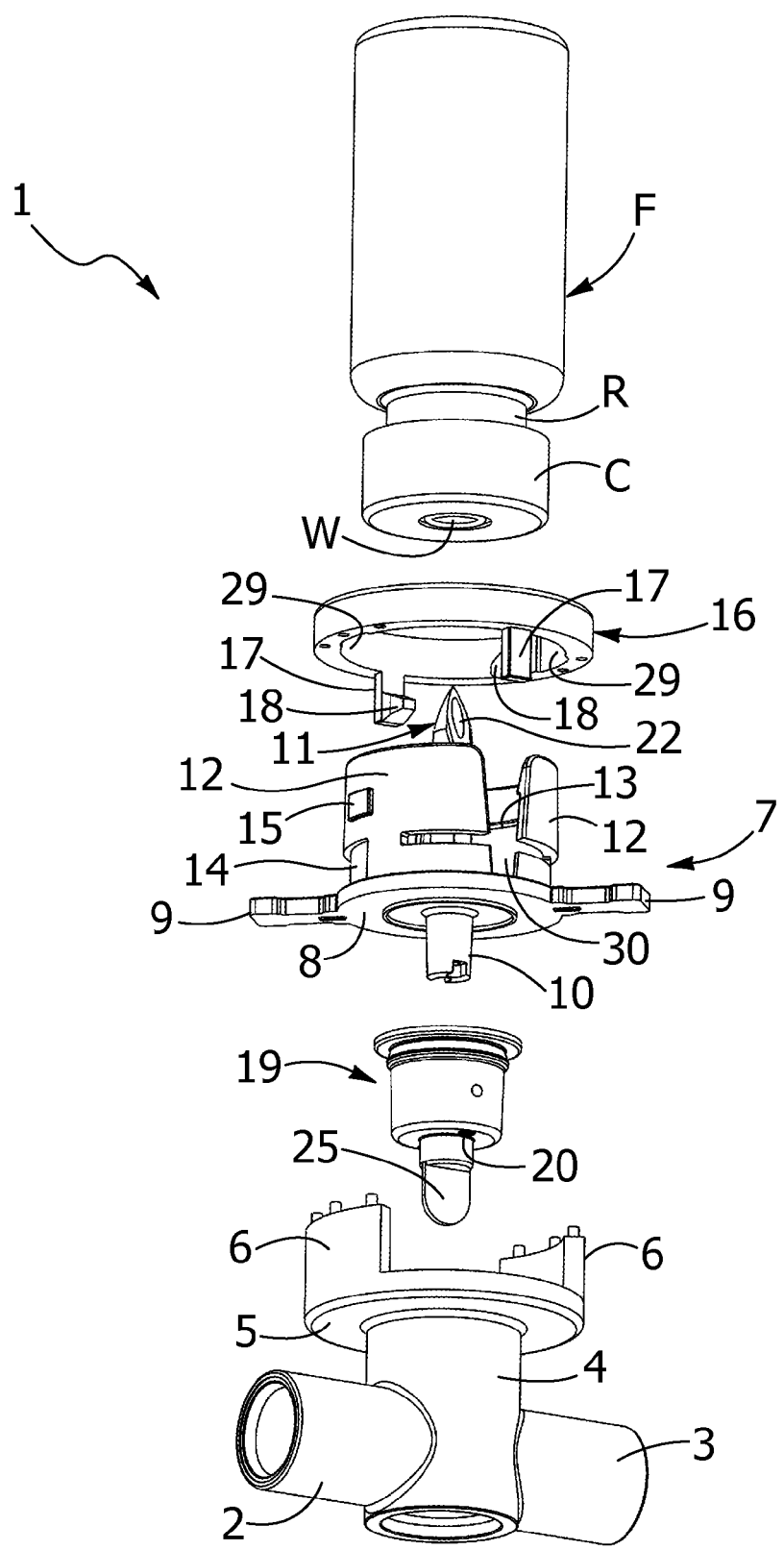
Figure 6:
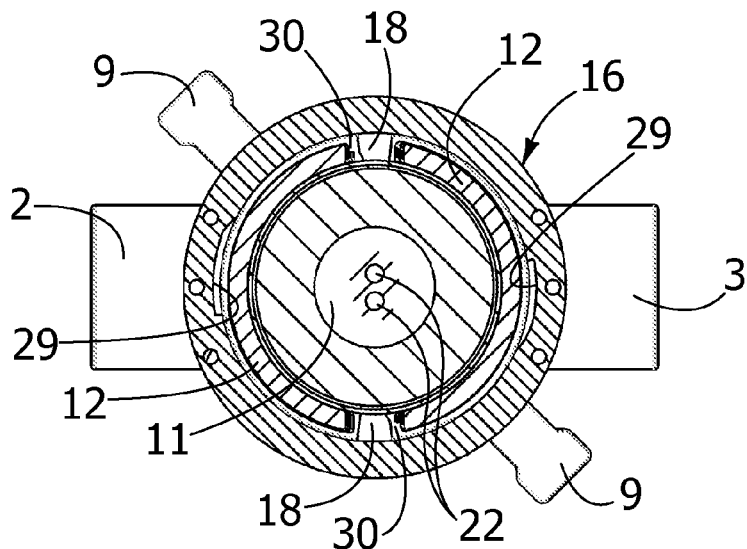
Figure 7:
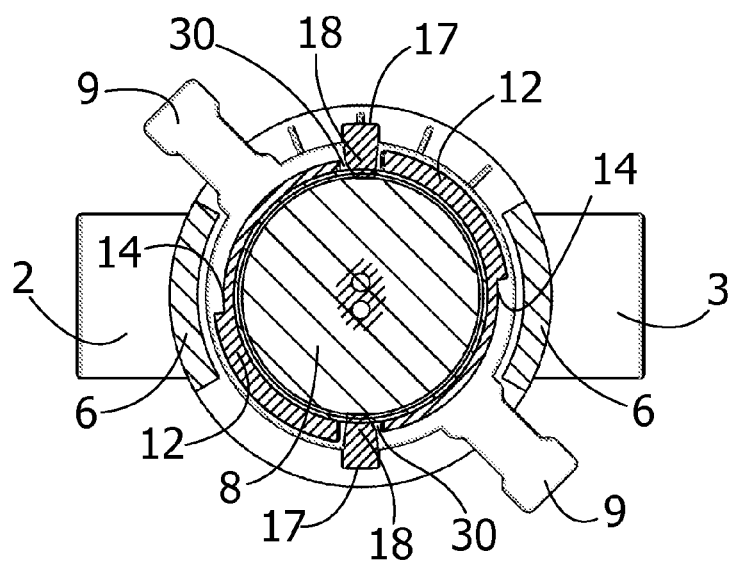
Figure 8:
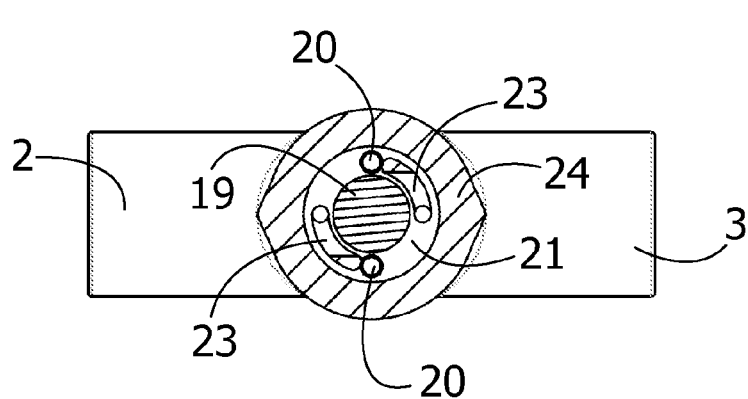
Figure 9:
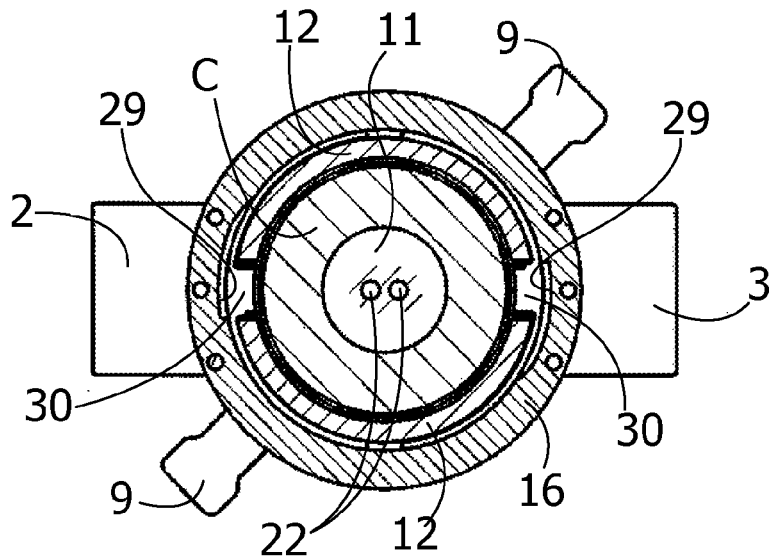
Figure 10:
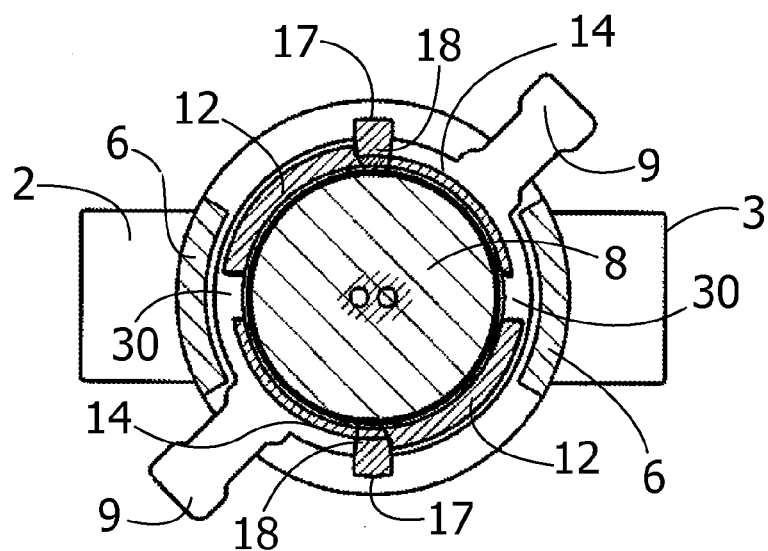
Figure 11:
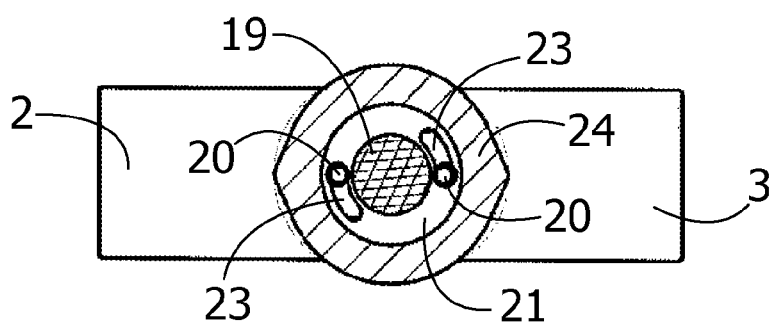
Figure 12:
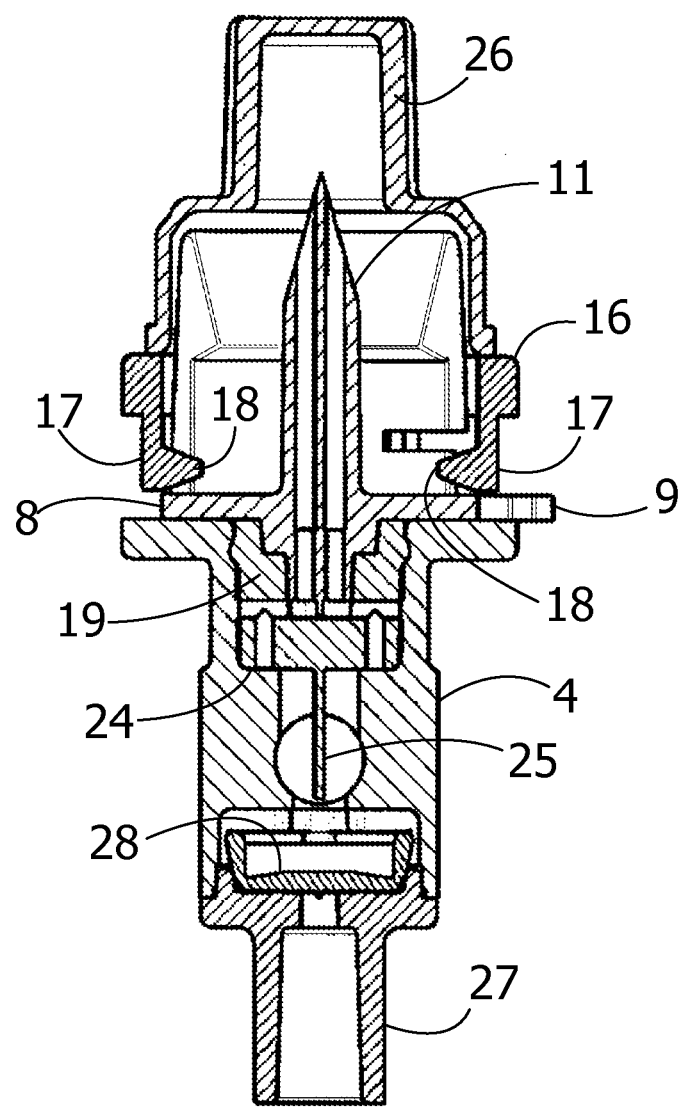

Now, the invention shall be described in detail, strictly for exemplifying and non-limiting purposes, with reference to the annexed representations, wherein:

FIG. 1 is a schematic perspective view of a device for controlled supply according to an embodiment of the invention, FIG. 2 is an elevational view of the device, FIG. 3 is an axial sectional view according to line III-III of FIG. 2, FIG. 4 is an axial sectional view according to line IV-IV of FIG. 3, FIG. 5 is an exploded perspective view of the supply device, FIGS. 6, 7 and 8 are transverse sectional views respectively according to lines VI-VI, VII-VII and VIII-VIII of FIG. 2, in a first operative condition of the device, FIGS. 9, 10 and 11 are views analogous to FIGS. 6, 7 and 8 in a second operative condition of the device, and FIG. 12 is a view analogous to FIG. 3 of a variant of the supply device according to the invention.

DETAILED DESCRIPTION OF THE INVENTION

Initially referring to FIGS. 1 and 2 a device according to the invention for the controlled supply of a liquid, contained within a bottle or vial F, ad a medical flow line (for example for haemodialysis) including a tubular inlet connector 2 and a tubular outlet connector 3 intended to be connected conventionally to respective ducts, is indicated in its entirety with reference 1.

Referring to FIG. 5, the bottle F is typically made of glass and comprises a neck C with an annular groove R and a pierceable end wall W, typically including a diaphragm made of elastomeric material or the like.

The supply device 1 is arranged at an intermediate tubular connector 4, arranged between the inlet and outlet connectors 2, 3 transverse thereto, by means of which an annular base 5, having a pair of lateral edges 6 juxtaposed and spaced therebetween, is formed.

A hollow retaining body mounted rotatable, through methods clarified hereinafter, on the annular base 5 is indicated in its entirety with 7. The retaining body 7 comprises a bottom wall lying on the annular base 5 and from which two diametrically opposite manoeuvre appendages 9 depart laterally.

A hollow axial stud 10 extends from the lower part of the bottom wall 8, and a hollow piercing spike 11 extends from the upper part thereof, coaxially to the stud 10 and in direct communication therewith. Furthermore, the upper part of the base wall 8 of the hollow body 7 has two elastically yielding jaws 12 mutually juxtaposed and spaced so as to delimit two radially opposite apertures 30 therebetween. Each jaw 12 has a continuous tooth projection 13 on the inner surface thereof a track recess 14 as well as a projecting relief 15, whose purpose shall be clarified hereinafter, on the outer surface thereof.

A ring fixedly secured to the top part of the edges 6 of the annular base 5 for the axial blocking of the retaining body 7 is indicated with 16. The ring 16 has a pair of elastically spreadable-apart diametrically opposite axial appendages 17 each of which bears, at the free end thereof, a radially projecting tooth 18 which has the purpose, clarified in detail hereinafter, of preventing the rotation of the retaining body 7 relative to the annular base 5 under given conditions.

The ring 16 is also formed, on the inner circumferential surface thereof, with a pair of juxtaposed recesses defining respective cam tracks whose purpose shall also be described hereinafter.

An element, for example made of elastomeric material fixed at the lower part to the bottom wall 8 of the hollow body 7 by means of the stud 10 and sealingly engaged, as represented in FIGS. 3 and 4, within the intermediate connector 4, is indicated with 19. Also as clearly observable in FIGS. 3 and 4, as well as in FIGS. 8 and 11, the body 19 is formed with two axial through bores 20 in communication, through a chamber 21 and the stud 10, with a pair of axial channels 22 of the hollow spike 11. The bores 20 are suitable to cooperate, as clarified hereinafter, with a pair of slits 23 (FIGS. 4, 8 and 11) of progressive depth formed at an annular flange 24 of the intermediate connector 4 and in communication with the flow line defined by the inlet and outlet connectors 2, 3. A blade appendage 25 of the body 19, which projects into the flow line defined by the inlet and outlet connectors 2, 3 is extended through the annular flange 24.

In the absence of the bottle F, the supply device 1 may be provided with a removable protection cap, indicated with 26 in FIG. 12, which shows a variant entirely identical to the aforedescribed embodiment except for the addition, on the side opposite to the intermediate connector 4, of a further tubular connector 27 connected to the flow line through the inlet and outlet connectors 2, 3 with the interposition of a check valve or an anti-siphon 28, for example of the type described and illustrated in the European patent EP-1661599B1 on behalf of the same applicant.

The supply device according to the invention operates as follows.

In the absence of the bottle F (and possibly in the presence of the protection cap 26) the stop teeth 18 of the retaining ring 16 are inserted into the apertures 30 between the two elastically yielding jaws 12 of the retaining body 16, which is thus blocked in rotation relative to the annular base 5 in a first angular position corresponding to that represented in FIGS. 6, 7 and 8. The appendages of the bottom wall 8, 9 are extended between the edges 6 of the annular base 5 and project therefrom so as to define two manoeuvre levers, and the reliefs 15 of the jaws 12 do not interfere with the cam tracks 29 formed on the inner surface of the ring 16. The bores 20 of the body 19 are misaligned relative to the slits 23 of the annular flange 24 of the intermediate connector 4, and blade 25 for spreading apart is positioned angularly as represented in FIGS. 3 and 4, i.e. in a substantially non-obstruction position of the flow line defined by the inlet and outlet connectors 2, 3. In this condition, a primary liquid flowing along such flow line cannot be placed in communication with the supply device 1, in that the rotation of the retaining body 7 which could place the slits 23 in communication with the bores 20 and thus with the ducts 22 of the hollow spike 11 it is hindered by the blocking action provided by the teeth 18 of the ring 16.

It is sufficient to secure the bottle F containing such secondary liquid to the supply device 1 in order to supply a secondary liquid into the flow line of the primary liquid. The neck C of the bottle F is then inserted axially into the retaining body 7, obtaining the piercing of the wall W thereof by the spike 11, as represented in FIGS. 3 and 4. Given that, during this step, the jaws 12 are free to be elastically spread apart from each other, the neck C is wedged between the respective tooth projections 13 which, at the end of the insertion travel of the bottle F, snap-sit into the annular groove R. The free end of the neck C of the bottle F is simultaneously wedged between the radial teeth 18 obtaining disengagement thereof, due to the elastic flexure of the legs 18, by the apertures 30. This frees the body 7 in rotation relative to the annular base 5, starting from the first angular position represented in FIGS. 6 to 8 (in which—as mentioned—the flow between the bores 20 of the body and the slits is closed), towards an angular position of complete opening represented in FIGS. 9 to 11, passing through a series of intermediate angular regulation positions. Such regulation may be executed by manually manoeuvring one and/or the other radial lever 9, also due to the help of possible reference marks provided on the annular base 5 between the edges 6 thereof. During the rotation of the retaining body 7 relative to the annular base 5 and the ring 16, enabled —as mentioned—following the elastic spreading apart of the radial teeth 18, such radial teeth 18 slide along the outer recesses 14 of the jaws 12. The reliefs 15 are simultaneously engaged in the cam tracks 29 so as to be countered by the ring 16 which prevents mutual elastic spreading apart thereof. Thus, the neck C of the bottle F is irreversibly retained in the retaining body 7, without possibility of inadvertent or intentional removal relative to the device 1.

The secondary liquid contained in the bottle F is thus supplied, through the ducts 22 of the hollow spike 11, the chamber 21, the bores 20 and the slits 23, into the primary liquid flow from the inlet connector 2 to the outlet connector 3. A slower or faster supply of the secondary liquid introduced into the primary liquid shall be obtained depending on the angular position of the retaining body 7 regulated by means of the levers 9.

During the rotation of the retaining body 7 the blade 25 also rotates between the non-obstruction position represented in FIGS. 3 and 4, corresponding to the angular position of complete closure of the, device, at a position of substantial obstruction in which it is arranged transverse relative to the primary liquid flow, corresponding to the angular position of complete opening of the device represented in FIGS. 9 to 11. The velocity of introduction of the secondary liquid into the primary liquid flow is thus progressively increased, passing from the non-obstruction position to the obstruction position of the blade 25, due to the increase of pressure within the bottle F generated by the primary liquid introduced therein through the channel 22 of the hollow spike 11 located upstream of the blade 25. Thus, the secondary liquid flows under pressure from the bottle F towards the other channel 22 of the hollow spike 11 located downstream of the blade 25.

At the end of supplying the secondary liquid, the bottle F may be finally removed after having returned the retaining body 7 to the initial angular position of FIGS. 6 to 9, i.e. after having closed the communication between such bottle F and the flow line between the inlet and outlet connectors 3, and having disengaged the outer reliefs 15 of the jaws 12 from the cam tracks 29 of the ring 16. Thus, this allows the jaws 12 to be elastically spreadable-apart to allow disengagement between the tooth reliefs 13 and the annular groove R of the bottle F.

Naturally, without prejudice to the principle of the invention, the details and embodiments may vary, even significantly, with respect to what has been described and illustrated without departing from the scope of the present invention, as defined in the claims that follow

The invention claimed is:

1. Device for the controlled supply of a medical liquid, including a tubular inlet connector and a tubular outlet connector defining a flow line of a primary fluid and an intermediate tubular transverse connector arranged therebetween for introducing into said flow line a secondary liquid contained within a bottle having a pierceable cap wherein said intermediate connector comprises an annular stationary base on which a hollow retaining body, into which said bottle is to be fitted, is rotatably arranged coaxially with said intermediate connector, said retaining body including: a hollow axial spike designed to pierce said pierceable cap when said bottle is fitted into said retaining body, said hollow spike having at least one inner flow passage, rotation blocking means of the retaining body relative to said base in a first angular position, said blocking means being disengageable by said bottle as a result of insertion thereof into said retaining body, stop means for axially retaining said bottle relative to said retaining body, said stop means activated following rotation of said retaining body starting from said first angular position, and progressive opening means of said flow passage of said hollow piercing spike towards said intermediate connector during the rotation of said retaining body from said first angular position, in which communication between said flow passage and said intermediate connector is completely closed, towards a second angular position in which such communication is completely open.

2. Device according to claim 1, further comprising a shifting member axially projecting from said retaining body, within said flow line, at the side opposite to said hollow spike and rotatable along with said retaining body between a position of substantial non-obstruction of the primary fluid flow, corresponding to said first angular position of the retaining body, and a position of substantial obstruction of the primary fluid flow, corresponding to said second angular position of the retaining body.

3. Device according to claim 2, wherein said flow passage of the hollow spike comprises two parallel ducts arranged on opposite sides relative to said shifting member.

4. Device according to claim 3, wherein said progressive opening means comprise a pair of variable-section passages formed in said intermediate connector and a pair of bores each communicating with a respective' duct of said hollow spike.

5. Device according to claim 4, wherein said bores are rotatable along with said retaining body to cooperate with said variable-section passages.

6. Device according to claim 1, wherein said axial stop means of the bottle include a pair of elastically-deformable juxtaposed jaws and cam means to keep said two jaws in elastically spreadable-apart condition in said first angular position of the retaining body and to rigidly retain said two jaws relative to said bottle following rotation of said retaining body between said first and said second angular position.

7. Device according to claim 6, wherein said rotation blocking means of the retaining body include a pair stop teeth carried by a ring fixedly secured to said base and engaged within respective apertures defined between said two jaws, said stop teeth being resiliently spreadable-apart relative to each other to disengage from said apertures as a result of insertion of said bottle into said retaining body.

8. Device according to claim 1, wherein said retaining body can be positioned at intermediate angular positions comprised between said first and said second angular position.

9. Device according to claim 8, wherein said retaining body is provided with at least one projecting lever to operate rotation thereof.

10. Device according to claim 2, wherein said shifting member is formed in an elastic material body sealingly rotatable within said intermediate connector.

11. Device according to claim 1, further comprising an auxiliary tubular connector coaxially juxtaposed to said intermediate connector and within which a check valve is fitted.

12. Device according to claim 1, further comprising a protection cap releasably secured to said retaining body.

13. System for the controlled supply of a medical liquid, comprising a bottle containing said liquid and having a pierceable cap, and a device having an inlet and an outlet defining a flow line of a primary fluid for introducing said liquid into said flow line, wherein said device comprises an annular stationary base on which a hollow retaining body, into which said bottle is to be fitted, is rotatably arranged coaxially with said base, said retaining body including:

a hollow axial spike designed to pierce said pierceable cap when said bottle is fitted into said retaining body, said hollow spike having at least one inner flow passage, rotation blocking means of the retaining body relative to said base in a first angular position, said blocking means being disengageabie by said bottle as a result of insertion thereof into said retaining body, stop means for axially retaining said bottle relative to said retaining body, said stop means activated following rotation of said retaining body starting from said first angular position, and progressive opening means of said flow passage of said hollow piercing spike towards said flow line during the rotation of said retaining body from said first angular position, in which communication between said flow passage and said flow line is completely closed, towards a second angular position in which such communication is completely open.

14. System according to claim 13, wherein said stop means of the bottle include a pair of elastically-deformable juxtaposed jaws and cam means to keep said two jaws in elastically spreadable-apart condition in said first angular position of the retaining body and to rigidly retain said two jaws relative to said bottle following rotation of said retaining body between said first and said second angular position.

15. System according to claim 14, wherein said rotation blocking means of the retaining body include a pair stop teeth carried by a ring fixedly secured to said base and engaged within respective apertures defined between said two jaws, said stop teeth being resiliently spreadable-apart relative to each other to disengage from said apertures as a result of insertion of said bottle into said retaining body.

16. System according to claim 14, wherein said retaining body can be positioned at intermediate angular positions comprised between said first and said second angular position.

17. System according to claim 14, wherein said retaining body is provided with at least one projecting lever to operate rotation thereof.

* * * * *